United States Patent [19]

Fujisaki

[11] Patent Number: 4,727,561

[45] Date of Patent: Feb. 23, 1988

[54] MEASURING APPARATUS AND METHOD EMPLOYING HARD X-RAYS

[76] Inventor: Yukio Fujisaki, 705, Daiichi-Kodan, 20-23, Hakataeki-mae 4-chome, Hakata-ku, Fukuoka-shi, Fukuoka 812, Japan

[21] Appl. No.: 865,014

[22] Filed: May 20, 1986

[30] Foreign Application Priority Data

May 24, 1985 [JP] Japan ............... 60-78312[U]

[51] Int. Cl.$^4$ ............................................. G01B 15/02
[52] U.S. Cl. ........................................ 378/54; 378/55; 378/56; 378/99; 378/158
[58] Field of Search ............... 378/99, 156, 157, 158, 378/54, 55, 56, 207; 358/111

[56] References Cited

U.S. PATENT DOCUMENTS 2,467,812  4/1949  Clapp .................................. 378/156
4,260,895  4/1981  Schitteahelm ..................... 378/157
4,639,943  1/1987  Heinze et al. ......................... 378/99

Primary Examiner—Janice A. Howell
Assistant Examiner—David P. Porta
Attorney, Agent, or Firm—Leydig, Voit & Mayer

[57] ABSTRACT

A measuring apparatus employing hard X-rays comprises a pair of sensors receiving substantially simultaneously hard X-ray beam emitted from an X-ray source, one of which sensors receives the beam directly from the source and not passed through an object to be measured while the other sensor receives the beam passed through the object. The other sensor comprises an X-ray image receiving camera providing an X-ray image of the object and a spot X-ray sensor for receiving the beam passed through a restricted measuring zone or spot in the object, and the camera and spot sensor are shiftable alternately to a position of receiving the beam passed through the object, whereby, after visual observation of the X-ray image for discrimination, the restricted zone or spot can be determined for a higher precision measuring, and a precise quantitative measurement can be carried out by the spot sensor with respect to the restricted zone or spot.

14 Claims, 12 Drawing Figures

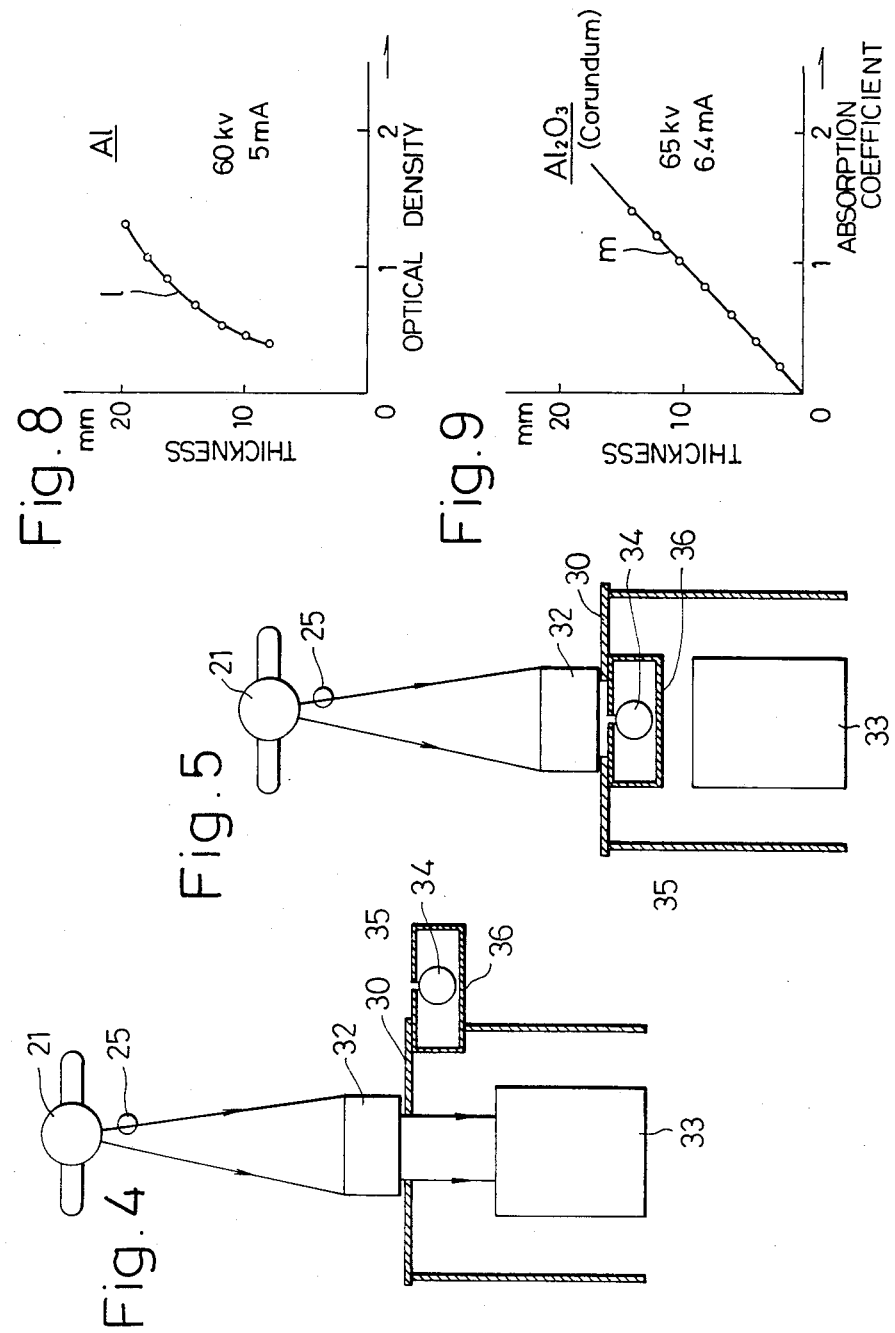

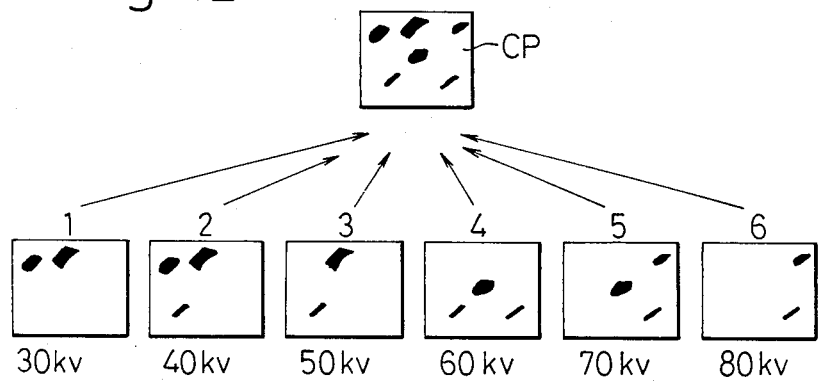
Fig. 12
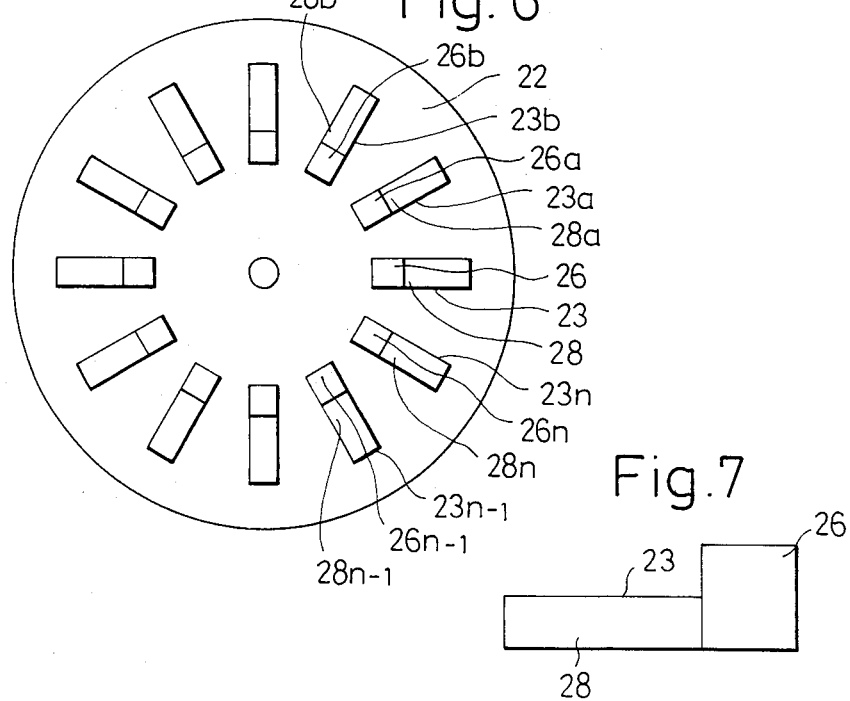
Fig. 6
Fig. 7

MEASURING APPARATUS AND METHOD EMPLOYING HARD X-RAYS

TECHNICAL BACKGROUND OF THE INVENTION

This invention relates to measuring apparatuses and methods employing hard X-rays and, more specifically, to such apparatus and method that realize quantitative measurement with a high detection accuracy utilizing so-called hard X-rays having short wavelengths below 1 Å, without an object being measured.

The hard X-ray measuring arrangement of the type referred to is effectively employed in such various fields as the medical field for diagnoses of internal organs, bones and teeth, in the industrial field for discrimination of various substances and materials and their deterioration, quality and the like inspections. This is and so on, because the arrangement allows the X-ray wavelength to be optionally selectable by varying applied voltage to X-ray source, the hard X-rays have extremely short in the wavelengths and are relatively safe for the human body while having very high penetrability. Thus, the object to be measured can be of any substance in any phase of gas, liquid, sol, gel, A to C stages in the plastics engineering, powder or solid.

DISCLOSURE OF PRIOR ART

In the field of measurement and inspection by means of X-rays, quantitative measurements have been long believed impossible with the use of the hard X-rays below 1 Å, even though their penetrability is increased. Hard X-rays below 1 Å have not been employed in the quantitative measurement and inspection.

The present inventor has noticed remarkable features of the hard X-rays such as having excellent penetrating characteristics, being less hazard to the human body, and being easy to shield from the human body. A result of studies and development by the inventor has been disclosed in Japanese Utility Model Appln. Laid-Open Publication No. 57-20648, according to which study quantitative measurements are realized by a double sensor mechanism comprising a pair of sensors for real time reception of hard X-rays from an identical X-ray source, one of which sensors directly receiving an X-ray beam from the source while the other sensor receiving an X-ray beam emitted from the same source but passed through an object to be measured.

This sensor mechanism has been satisfactory for discriminating, for example, whether or not a jewel or the like is real one, but needs a broader range for observation and higher measuring accuracy. These improvements are needed for highly precise analytical measurement of substances or materials, in particular, inspection of delicate or minute metallic fatigue, fatigue, measurement for determination of deterioration or available life time, and the like.

TECHNICAL FIELD OF THE INVENTION

A primary object of the present invention is, therefore, to provide a measuring apparatus and method which are based on a novel hard X-ray measuring technique of the present inventor which can greatly remarkably improve the measuring accuracy and can broaden the range of objects to be measured.

According to the present invention, this object is attained by providing a measuring apparatus comprising a pair of first and second sensor means capable of receiving hard X-rays from an identical X-ray source, the first sensor means directly receiving the hard X-rays from the source while the second sensor means receiving the hard X-rays from the same source and passed through an object to be measured on a table disposed below the source, the intensity of the hard X-rays detected by the first sensor means being used as a reference value for executing a quantitative measurement by means of the hard X-rays, wherein the table carrying thereon the measuring object is provided to be shiftable, and the second sensor means comprises an X-ray image receiving camera and a spot X-ray sensor which are relatively shiftable alternately to a zone of receiving the hard X-rays from the X-ray source.

According to this arrangement, the image receiving camera receives the rays passing through the measuring object to provide an X-ray image of the object. The received image permits observation of structure or composition of the object in order to determine a zone or spot requiring a precise measurement or inspection. Thereafter the spot X-ray sensor is disposed at the thus determined precise measurement zone or spot for executing the precise measurement or inspection, so that a quantitatively measuring function with a high resolution as well as a higher precision measurement requiring only a relatively short time can be attained.

Other objects and advantages of the present invention shall be made clear in the following description of the invention detailed with reference to a preferred embodiment shown in accompanying drawings.

BRIEF EXPLANATION OF THE DRAWINGS

FIG. 4 schematically shows a relative arrangement of only the X-ray image receiving camera and spot X-ray sensor in the measuring apparatus of FIG. 1 which the camera at the energized state;

FIG. 5 also schematically shows the relative arrangement of only the camera and spot X-ray sensor in the apparatus of FIG. 1 but with the spot X-ray sensor at the energized position;

FIG. 6 is a plan view of a filter disc in the measuring apparatus of FIG. 1;

FIG. 7 is a schematic cross-sectional view of a filter member mounted on the filter disc of FIG. 6;

FIG. 8 is a graph showing relationship between the optical density of aluminum object measured by a known film method and the thickness of the object;

FIG. 9 is a graph showing relationship between the absorption coefficient of the hard X-rays and the thickness of an object of corundum measured according to the present invention;

FIG. 12 are explanatory views of showing an example of utilizing the X-ray images obtained by the measuring apparatus of FIG. 1.

Figure 1:
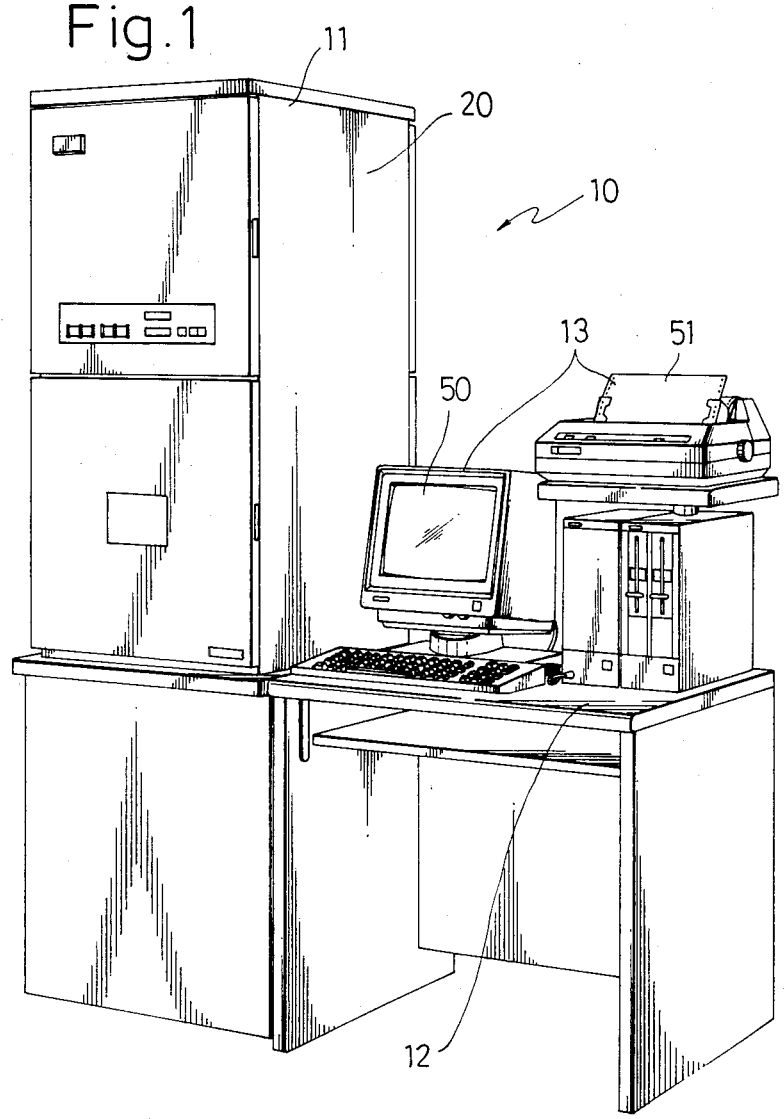
FIG. 1 is a perspective view showing an overall elevation of the apparatus employing the hard X-rays according to the present invention.

While the present invention shall now be described with reference to the preferred embodiment shown in the drawings, it should be understood that the intention is not to limit the invention only to the particular embodiment shown but rather to cover all alterations, modifications and equivalent arrangements possible within the scope of appended claims.

DISCLOSURE OF PREFERRED EMBODIMENT

Referring to FIGS. 1 to 7, there is shown a measuring apparatus 10 employing hard X-rays according to the present invention, which comprises a measuring station 11, an operating/processing station 12 including a computer, and a display station 13. Disposed in the upper part of an X-ray shielding housing 20 of the measuring station 11 is an X-ray source 21 for emitting hard X-rays of wavelengths less than 1 Å, and below the X-ray source a rotary filter disc 22 is located. This rotary filter disc 22 carries a plurality of filter members 23, 23a, 23b, ... 23n (FIG. 6) arranged as mutually spaced circumferentially to radially extend so that, when the disc 22 is properly rotated by a rotary driving unit 24, one of the filter members 23, 23a, 23b, ... 23n can be positioned immediately below the X-ray source. The filter members 23, 23a, 23b, ... 23n are made mutually different in their filtering function so as to correspond to different voltages applied to the X-ray source 21. The respective filter members comprise a first filter part 26, 26a, 26b, ... or 26n which is disposed in the disc 22 radially inward for use with respect to a first sensor means 25, and a second filter part 28, 28a, 28b, ... or 28n disposed radially outward for use with respect to a second sensor means 27.

The first sensor means 25 is located below the rotary filter disc 22 to receive a hard X-ray beam emitted from the source 21 directly and only penetrating through one of the first filter parts 26, 26a, 26b, ... 26n of the filter members and passing through a slit 29 of a slit member positioned between the disc 22 and the sensor 25, but without penetrating through a later described object 32 to be measured.

Further disposed right under the X-ray source 21 and rotary filter disc 22 within the housing 20 is a table 30 for carrying thereon and across an aperture the object 32 to be measured, and this table 30 is coupled to a driving unit 31 to be freely shiftable in x, y and z directions. The second sensor means 27 is located below the table 30 to receive the hard X-ray beam penetrating through the aperture in the table 30, comprises an X-ray sensor 34. In the illustrated embodiment, the X-ray image receiving camera 33 is disposed fixedly under the table 30, whereas the spot X-ray sensor 34 is disposed shiftable between a position below the object 32 and within the X-ray beam penetrating therethrough and the other position out of the beam, as provided within a casing 36 having an upward spot aperture 35 for passing the beam to the sensor 34 and coupled to a driving unit 37 for the shifting of the casing reciprocally between the two positions. Accordingly, the image receiving camera 33 and spot X-ray sensor 34 are arranged to be relatively alternately positioned at the position for receiving the hard X-ray beam reached through one of the second filter parts 28, 28a, 28b, ... 28n and the object 32, by means of, in the present instance, the reciprocal shifting of the casing 36 of the sensor 34.

In the operating/processing station 12, on the other hand, a first control means 40 applies through a transformer 38 to the X-ray source 21 an electric power of a voltage predetermined in accordance with the composition or the like of the measuring object 32 to set the intensity, i.e., the penetrability of the X-rays suitable for object. In the present instance, the rotary driving unit 24 for the filter disc 22 is arranged to be energized also by the first control means 40, so that one of the filter members 23, 23a, 23b, ... 23n in the rotary filter disc 22 which corresponds to the voltage applied to the X-ray source 21 will be indexed to be at a position of passing the emitted X-rays. The driving unit 31 for the table 30 is controlled by a second control means 41 to have the table shifted in the three-dimentional directions, whereas the driving unit 37 for the spot X-ray sensor 34 is controlled by a third control means 42 to have the sensor reciprocally shifted with the casing 36. These first to third control means 40 to 42 are connected to a computer 43 disposed within the station 12 for providing proper outputs to the respective control means for their energization. The first sensor means 25 as well as the spot X-ray sensor 34 of the second sensor means 27 are connected to an operational means 44 which is provided within the operating/processing station 12 and connected to the computer 43 to operate a logarithmic value of a ratio between detection signals of the both sensors 25 and 34. Further, the image receiving camera 33 of the second sensor means 27 is connected to a signal processing means 45 which generates X-ray image signals.

The computer 43 is connected to a video scope means 50 provided in the display station 13 for receiving the logarithm outputs obtained from the both sensors 25 and 34 or X-ray image outputs from the image receiving camera 33 to visualize a required information. In this case, the X-ray image from the image receiving camera 33 may be separately displayed on another scope means directly connectable to the signal processing means 45.

In addition, the first and second filter parts 26–26n and 28–28n of the filter members 23–23n of the rotary filter disc 22 are so selected that an expression of the relation between the thickness of the object 32 to be measured and the absorption coefficient of the hard X-ray or, in other words, the optical density will be drawn by a straight line on a diagram of x and y orthogonal coordinates. For example, a diagram of FIG. 8 shows that the relation of the optical density measured by the known film method to the thickness of the object with the X-ray source energized by a power of 60 KV and 5 mA could have been expressed only by a curve "1" of FIG. 8 and the method has been not suitable for the quantitative measurement, whereas a diagram of FIG. 9 shows that the absorption coefficient to the thickness relation in a measurement performed according to the present invention with respect an object of corundum with the X-ray source energized by a power of 65 KV and 6.4 mA is expressed by a straight line "m" and the invention is suitable for realizing the quantitative measurement.

In the operational means 44 receiving the detection outputs of the first sensor means 25 and spot X-ray sensor 34 of the second sensor means 27, a so-called zero balance is kept, in such that a logarithm log n(Y/Z) of a ratio between a detection output Y indicative of the X-ray intensity at the first sensor means 25 and a detection output Z indicative of the X-ray intensity at the spot X-ray sensor 34 becomes zero.

Figure 2:
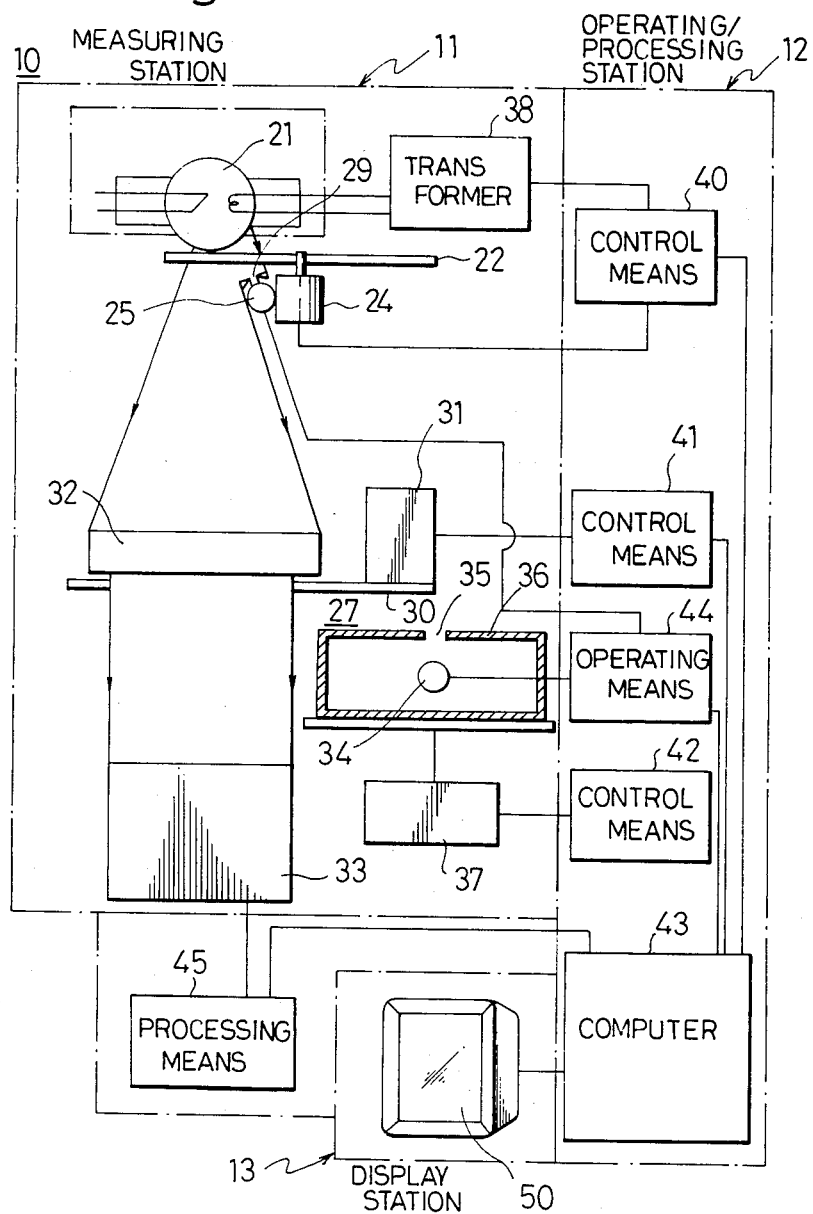
FIG. 2 is a schematic block diagram showing a part of the apparatus of FIG. 1 with the X-ray image receiving camera shown at energized state.
Figure 3:
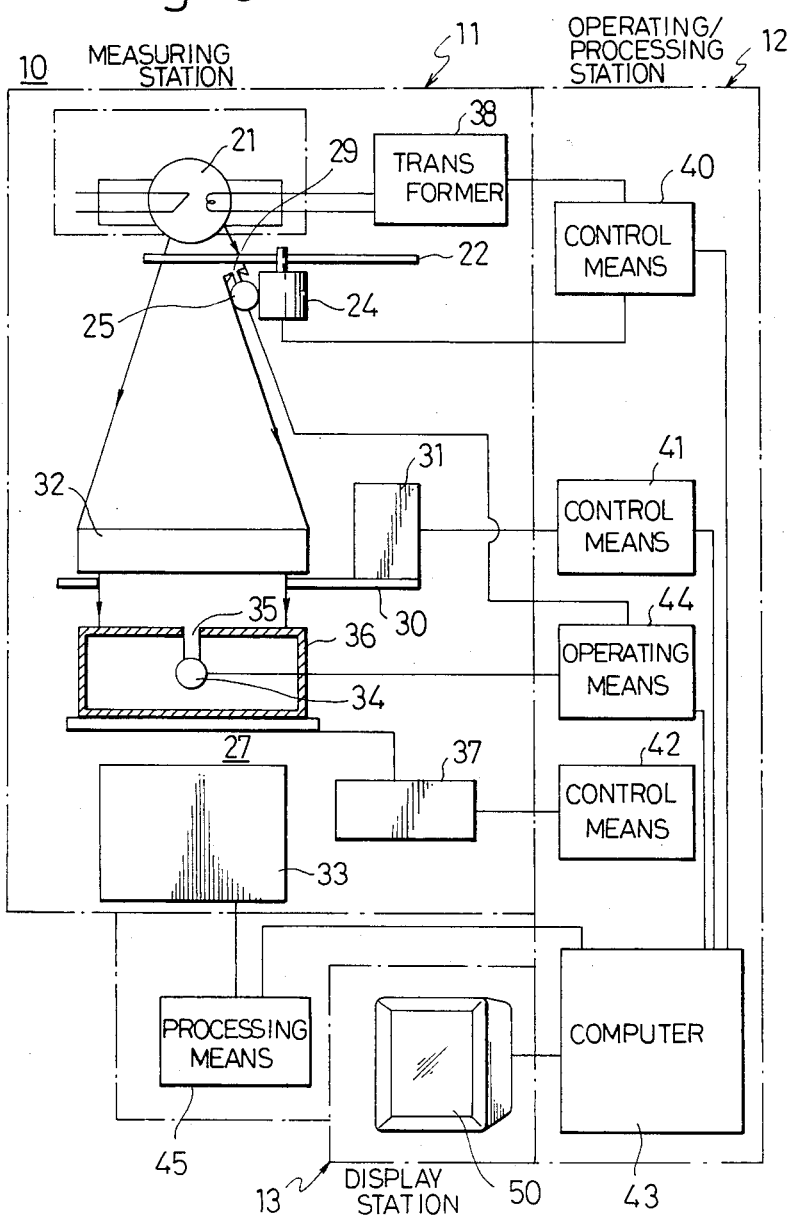
FIG. 3 is a schematic block diagram similar to FIG. 2 but with the spot X-ray sensor shown as shifted to energized position in the apparatus of FIG. 1.

The operation of the measuring arrangement of the present invention shall now be described in detail. Now, assume as shown in FIG. 2 that the spot X-ray sensor 34 in the second sensor means 27 is located at its OFF position, that is, out of the position of receiving the hard X-ray beam from the X-ray source 21 energized. Then, the hard X-rays emitted penetrate through one of the second filter parts of the filter members 23, 23a, 23b, . . . 23n in the rotary filter disc 22 and through the measuring object 32 on the table 30 to be incident on the image receiving camera 33. In this case, an operator observes the X-ray image provided by the camera 33 on the scope 50 of the display station 13 while properly operating, for example, the computer 12 to optionally increase or decrease the voltage applied to the X-ray source 21 through the first control means 40, with the rotary driving unit 24 thus energized by the first control means 40 to index and position suitable one of the filter members immediately below the X-ray source 21 depending on the increased or decreased voltage to the source. As required, the driving unit 31 is operated through the second control means 41 to shift the table 30 three-dimentionally in the x, y and z directions, freely within three dimensional space, so as to position the measuring object 32 on the table properly for obtaining a desired X-ray image for a precise observation.

From the X-ray image on the scope 50, the operator visually selects a zone or spot of the object where a higher precision measurement appears necessary, and he inputs positional information of the selected zone or spot into a memory of the computer 43 in terms of the x and y coordinates, while deenergizing the image receiving camera 33. Then, the driving unit 37 is driven through the third control means 42 by means of the computer 43 to shift the casing 36 to position its spot X-ray sensor 34 here energized, the first sensor means 25 detects directly the hard X-ray beam from the X-ray source 21 passed only through one of the first filter parts of the filter members 23, 23a, 23b, . . . 23n and generates the detecion output Y, and at the same time the spot X-ray beam from the X-ray source 21 passed through one of the second filter parts of the filter members 23, 23a, 23b, . . . 23n and through the higher precision measuring zone or spot of the object 32 to generate the detection output Z, the both of which outputs Y and Z are provided to the operational means 44, where the logarithm log n(Y/Z) of a ratio between the both detection outputs Y and Z, that is, between the intensities of the hard X-rays at the both sensors 25 and 34 is calculated and a calculated value is divided by the thickness of the object 32 to obtain the linear absorption coefficient ($\mu$) of the hard X-rays.

The obtained linear absorption coefficient ($\mu$) is displayed on the scope 50 by the computer 43. In this case, the value of the linear absorption coefficient ($\mu$) may be printed by a printer 51 of the display station 13, together with information related to the object preliminarily given to the computer 43.

As has been described above, according to the present invention, the quantitative measurement can be realized by contrasting with each other the both intensities of the hard X-rays as detected directly by the first sensor means 25 and as detected at the spot sensor 34 of the second sensor means 27 after penetrating through the object 32, and additionally, by taking the logarithm of the ratio between the both detection values, the both detection values at the first and second sensors can be made accurately in proportional relation or, in other words, the logarithm log n(Y/Z) of the ratio between the both detection values can be made substantially linear when expressed with such graph as in FIG. 9, whereby the measurement read-out can be made easy and the measurement certainty can be well elevated. It has been found that, according to the present invention, the measurement accuracy can be kept to be within ±0.005 in terms of the absorption coefficient ($\mu$) of the hard X-rays.

Detailed explanation of practical measuring examples shall now be made. A ceramic ($Al_2O_3$) plate of 10.12 mm thick was used as the measuring object 32 and a plurality of scratches were intentionally given to the ceramic to form cavities therein. The object was measured with the hard X-rays while varying the voltage to the X-ray source 21, and observing the X-ray image on the display obtained by the X-ray image receiving camera 33 of the second sensor means 27. As a result, portions different in the optical density which could be presumed as being the cavities have been visually recognized in the X-ray image under an application of the power of 70 KV and 10 mA. Subsequently, after deenergization of the X-ray image receiving camera 32, the voltage and current were changed to 64 KV and 6 mA respectively, the casing 36 was shifted to the position immediately below the object 32 with the spot X-ray sensor 34 energized, the object 32 was moved with the table 30 driven by the driving unit 31 energized so as to be measured at 9 points at regular intervals of 0.5 mm by the spot X-ray sensor 34, and following results were obtained in terms of the linear absorption coefficient ($\mu$) of the hard X-rays:

| Measuring Points | Linear Absorption Coefficient ($\mu$) |
| --- | --- |
| 1 | 1.3273 |
| 2 | 1.3644 |
| 3 | 1.3344 |
| 4 | 1.3626 |
| 5 | 1.3517 |
| 6 | 1.3650 |
| 7 | 1.3622 |
| 8 | 1.3577 |
| 9 | 1.3634 |

Accordingly, it has been found that, where there exists the cavity in the object, the linear absorption coefficient ($\mu$) becomes small, and the size "x" of the cavity is derived from an equation $$x = (1 - \mu 1/\mu a)d$$

wherein "d" is the thickness of the object, $\mu 1$ is the absorption coefficient at a point of the object where the cavity exists and $\mu a$ is the absorption coefficient at a point where no cavity exists. When the thickness "d" of 10.12 mm, $\mu 1$ of 1.3273 at the measuring point 1, and $\mu a$ of 1.3610 as an average value of the measured values at the points 2 and 4 to 9 are placed in the equation, then the result will be $$x = (1 - 1.3273/1.3610)10.12 = 250 \ (\mu m)$$

and it is judged that the size of the cavity is about 250 ($\mu$m).

Figure 10:
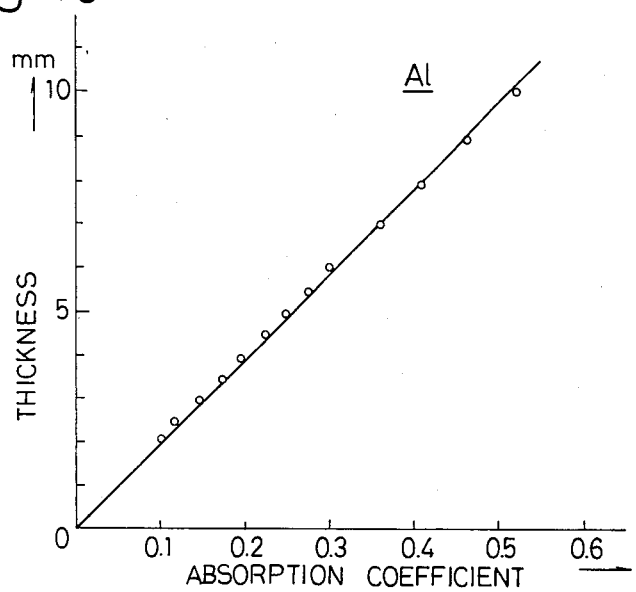
FIG. 10 is a graph showing the relationship between the absorption coefficient of the hard X-rays and the thickness of the aluminum object measured according to the present invention.
Figure 11:
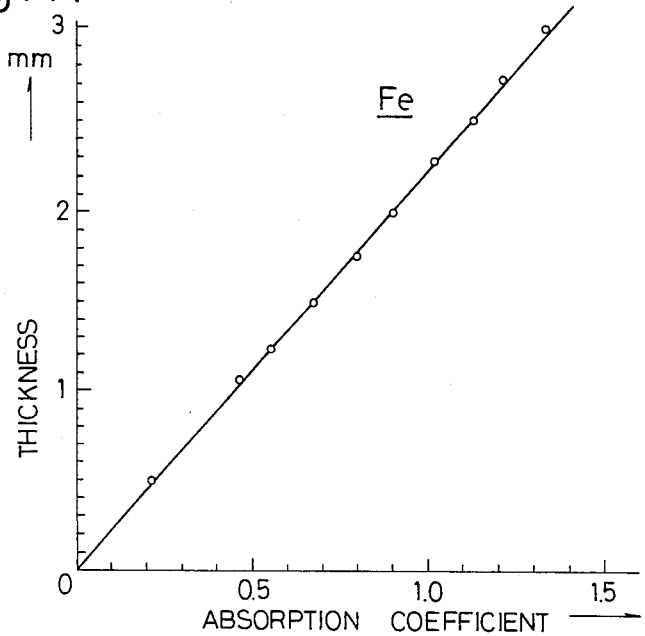
FIG. 11 is a graph showing relationship between the absorption coefficient of the hard X-rays and the thickness of an object of iron measured according to the present invention.

Further, sheet materials of aluminum respectively having the same quality but different thicknesses, and those of iron, were subjected to the hard X-ray measurement of the absorption coefficient ($\mu$). When the actually measured values of the respective aluminum and iron sheets were plotted on x and y coordinates and connected together, it has been found that the plots for the aluminum or iron sheets were substantially on a straight line as shown in FIG. 10 or 11, that is, the log n(Y/Z) values were accurately proportional.

The present invention may be modified in various ways. For example, although the description has been made to that the image receiving camera 33 of the second sensor means 27 is stationary and the spot X-ray sensor 34 is shiftable, they may be disposed oppositely in such that the camera 33 is shiftable and the spot X-ray sensor 34 is stationary. Further, the camera 33 and sensor 34 may even be both shiftable, or both stationary but with the X-ray source 21 disposed shiftable.

It is further possible that, when the X-ray image from the camera 33 is recorded on, for example, video tapes upon each change of the applied voltage to the X-ray source 21 sequentially from 30 to 80 KV and these recorded images are reproduced as overlapped as shown in FIG. 12, a three-dimensional image CP can be provided for precise visual observation. In this case, a lower applied voltage to the X-ray source 21 provides an image for the composition of a smaller atomic number in the object, and a higher applied voltage provides an image of a larger atomic number composition, so that the overlapped reproduction of these recorded images will allow a simultaneous observation of the compositions ranging from the low atomic number to the large atomic number to be made.

What is claimed as my invention is:

1. An X-ray measuring apparatus comprising:
   first sensor means for directly receiving hard X-rays from an X-ray source,
   a movable table disposed below said X-ray source for carrying thereon an object to be measured, and
   second sensor means for receiving said hard X-rays from the X-ray source penetrated through the object to be measured, said second sensor means including
   an X-ray image receiving camera, and
   a spot X-ray sensor, said camera and spot X-ray sensor being relatively shiftable alternately to a position of receiving said hard X-rays emitted from said X-ray source and penetrated through the object, and
   filter means disposed at a position between said X-ray source and said first and second sensor means, said filter means having a first filter part for the first sensor means and a second filter part for the second sensor means, said first and second filter parts being so set that the relation between the thickness of said object and the absorption coefficient of said hard X-rays can be expressed substantially as a linear function.

2. An apparatus according to claim 1 further comprising means for providing a three-dimensional image of the object.

3. An apparatus according to claim 1, wherein said filter means is a rotary filter disc, said first and second filter parts respectively comprise a plurality of filtering members arranged in said disc as mutually circumferentially spaced and each corresponding to each of different voltages selectively applied to said X-ray source, said rotary filter disc being rotated to index one of said filtering members which corresponds to said voltage selected and applied to the source to be at said position between the source and said first and second sensor means.

4. An apparatus according to claim 3 wherein said table is provided to be three-dimensionally movable in three x, y and z directions.

5. An apparatus according to claim 4 wherein said spot X-ray sensor is provided within a casing having a spot aperture through which said hard X-rays are passed, said casing being reciprocally shiftable with said spot X-ray sensor into and out of a position of receiving the hard X-rays penetrated through said object.

6. An apparatus according to claim 4 which further comprises an operating/processing station including at least first and second control means and a computer cooperating with said first and second control means for operating said rotary filter disc through said first control means and said table through said second control means.

7. An apparatus according to claim 1 which further comprises an operating/processing station including an operational means which receives first detection signal of said first sensor means and second detection signal of said spot X-ray sensor in said second sensor means and a computer operatively associated with said operational means, said operational means operating a logarithmic value of a ratio between said first and second detection signals.

8. An apparatus according to claim 7 which further comprises a display station for displaying said second detection signal of said second sensor means.

9. An apparatus according to claim 8 wherein said display station includes scope means for displaying thereon an X-ray image of said object from said X-ray image receiving camera.

10. An apparatus according to claim 9 wherein said display station is operatively associated with said operating/processing station.

11. An apparatus according to claim 10 wherein said display station further includes a printer.

12. A method for X-ray measuring an object employing hard X-rays comprising the steps of:
    emitting said hard X-rays from an X-ray source,
    receiving at a first sensor means hard X-rays emitted from said X-ray source and not penetrating through said object,
    emitting hard X-rays from the X-ray source so as to penetrate through said object while moving the object,
    receiving at a second sensor means said hard X-rays penetrated through the object,
    obtaining a ratio between a reference intensity of the hard X-rays detected at said first sensor means and intensity of the hard X-rays detected at said second sensor means, and obtaining the relation between a thickness of said object and hard X-ray absorption coefficient so that said relation can be expressed as substantially a linear function,
    wherein said step of receiving the hard X-rays penetrated through the object at the second sensor means further includes a step of alternately executing a detection of an X-ray image of the object and a highly precise detection with respect to a restricted part of the object.

13. A method according to claim 12 further comprising the step of forming a three-dimensional image of the object.

14. A method according to claim 12 wherein said step of obtaining said intensity ratio includes a step of taking a logarithmic value of said ratio.

* * * * *